United States Patent
Alicot et al.

(10) Patent No.: US 9,792,129 B2
(45) Date of Patent: Oct. 17, 2017

(54) NETWORK RANGE EXTENDER WITH MULTI-RF RADIO SUPPORT FOR PLURALITY OF NETWORK INTERFACES

(71) Applicants: Jorge Alicot, Davie, FL (US); Paul B. Rasband, Lantana, FL (US)

(72) Inventors: Jorge Alicot, Davie, FL (US); Paul B. Rasband, Lantana, FL (US)

(73) Assignee: Tyco Fire & Security GmbH, Neuhausen am Rheinfall (CH)

( * ) Notice: Subject to any disclaimer, the term of this patent is extended or adjusted under 35 U.S.C. 154(b) by 189 days.

(21) Appl. No.: 14/463,980

(22) Filed: Aug. 20, 2014

(65) Prior Publication Data

US 2015/0249928 A1 Sep. 3, 2015

Related U.S. Application Data

(60) Provisional application No. 61/973,962, filed on Apr. 2, 2014, provisional application No. 61/946,054, filed on Feb. 28, 2014.

(51) Int. Cl.
*H04W 24/02* (2009.01)
*G06F 9/44* (2006.01)
(Continued)

(52) U.S. Cl.
CPC ............ *G06F 9/4416* (2013.01); *A61B 17/00* (2013.01); *G01S 5/02* (2013.01); *G01S 5/0236* (2013.01); *G01S 5/0284* (2013.01); *G01S 13/765* (2013.01); *G06F 8/63* (2013.01); *G08B 7/062* (2013.01); *G08B 7/066* (2013.01); *G08B 13/19613* (2013.01); *G08B 13/19697* (2013.01); *G08B 25/007* (2013.01);
(Continued)

(58) Field of Classification Search
None
See application file for complete search history.

(56) References Cited

U.S. PATENT DOCUMENTS 7,003,291 B2 * 2/2006 Zhnag ................... H04W 84/14
455/424
7,689,221 B1 * 3/2010 Gazzard ................. H04L 47/10
455/436
(Continued)

FOREIGN PATENT DOCUMENTS

FR EP 1718095 A1 * 11/2006 ............ H04W 36/14
WO WO 01/06401 1/2001
WO WO 2013/159217 10/2013

OTHER PUBLICATIONS

International Search Report and Written Opinion, PCT/US15/17680.
International Search Report and Written Opinion, PCT/US15/17702.

*Primary Examiner* — Alex Skripnikov
(74) *Attorney, Agent, or Firm* — Fish & Richardson P.C.

(57) ABSTRACT

A networked system for managing a physical intrusion detection/alarm includes a network of end nodes, e.g., sensor nodes including one or more constrained sensor nodes for sensing physical conditions, and a gateway to provide network connections for the constrained sensor nodes. The system also includes a range extender for connecting the one or more constrained sensor nodes to the gateway, with the range extender including first and second radios and corresponding processors to wirelessly communicate with the gateway and constrained nodes.

18 Claims, 7 Drawing Sheets

(51) Int. Cl.

| | | |
|---|---|---|
| *G06F 9/445* | (2006.01) | |
| *H04L 12/46* | (2006.01) | |
| *H04L 12/26* | (2006.01) | |
| *H04N 5/232* | (2006.01) | |
| *H04N 5/76* | (2006.01) | |
| *H04W 16/26* | (2009.01) | |
| *H04L 12/64* | (2006.01) | |
| *H04L 29/08* | (2006.01) | |
| *H04L 29/12* | (2006.01) | |
| *A61B 17/00* | (2006.01) | |
| *G01S 5/02* | (2010.01) | |
| *G01S 13/76* | (2006.01) | |
| *G08B 7/06* | (2006.01) | |
| *G08B 13/196* | (2006.01) | |
| *G08B 25/00* | (2006.01) | |
| *H04L 9/00* | (2006.01) | |
| *H04W 8/26* | (2009.01) | |
| *H04W 92/02* | (2009.01) | |

(52) U.S. Cl.
CPC ............ *G08B 25/009* (2013.01); *H04L 9/004* (2013.01); *H04L 12/4625* (2013.01); *H04L 12/6418* (2013.01); *H04L 43/0876* (2013.01); *H04L 61/106* (2013.01); *H04L 67/12* (2013.01); *H04L 67/34* (2013.01); *H04N 5/23241* (2013.01); *H04N 5/76* (2013.01); *H04W 8/26* (2013.01); *H04W 16/26* (2013.01); *H04W 24/02* (2013.01); *G08B 13/19671* (2013.01); *H04L 43/0805* (2013.01); *H04L 61/6013* (2013.01); *H04L 61/6072* (2013.01); *H04W 92/02* (2013.01)

(56) References Cited

U.S. PATENT DOCUMENTS

| | | | |
|---|---|---|---|
| 7,804,849 B2* | 9/2010 | Mahany | H04L 1/0002 370/230 |
| 7,966,660 B2* | 6/2011 | Yermal | H04L 63/1416 726/22 |
| 2007/0147425 A1* | 6/2007 | Lamoureux | H04W 88/02 370/469 |
| 2007/0239350 A1 | 10/2007 | Zumsteg et al. | |
| 2008/0068267 A1 | 3/2008 | Huseth et al. | |
| 2011/0051656 A1 | 3/2011 | Hethuin et al. | |
| 2011/0310791 A1 | 12/2011 | Prakash et al. | |
| 2013/0003645 A1 | 1/2013 | Shapira et al. | |
| 2013/0035090 A1* | 2/2013 | Moshfeghi | H04W 88/04 455/422.1 |
| 2013/0064233 A1 | 3/2013 | Hethuin et al. | |

\* cited by examiner

NETWORK RANGE EXTENDER WITH MULTI-RF RADIO SUPPORT FOR PLURALITY OF NETWORK INTERFACES

CLAIM OF PRIORITY

This application claims priority under 35 U.S.C. §119(e) to provisional U.S. Patent Application 61/973,962, filed on Apr. 2, 2014, entitled: "Wireless Sensor Network", and provisional U.S. Patent Application 61/946,054, filed on Feb. 28, 2014, entitled: "Wireless Sensor Network", the entire contents of which are hereby incorporated by reference.

BACKGROUND

This description relates to operation of network security systems in particular intrusion systems that are wireless and include range extenders.

Wireless sensor network/wireless device based data collection systems with remote server-based monitoring and report generation are becoming more common in applications such as home safety monitoring, electrical and water utility meter monitoring, and human and asset tracking. For example, it is common for businesses and homeowners to have a security system for detecting alarm conditions at their premises and signaling the conditions to a monitoring station or to authorized users of the security system.

Traditional low-power network range extenders multiplex between an end node side and an access point side of a network. This architecture can be limiting, particularly for energy harvesting and battery operated devices. Such an architecture can be unpredictable and wasteful of available communication bandwidth.

SUMMARY

Described herein are techniques for communication systems implemented using a range extender having a split architecture. In this split architecture, independent radios interface to different sides of the range extender on a wireless network, and one or more processors control a corresponding radio or radios. In some implementations, radios can be distributed across network communication channels based on network deployment needs (e.g., for energy sensitive devices or mains power). Furthermore, a radio/processor may be configured to take on multiple behaviors in managing the network. Still further, described herein is the communication of activity and parameters between radios to manage the network.

According to an aspect, an apparatus for use in a network that includes an access point and an end node includes a first radio to wirelessly communicate with the access point, a first processing device programmed to control and process messages received from the first radio, a second radio to wirelessly communicate with the end node, and a second processing device programmed to control and process messages received from the second radio and wherein the first and second processing devices are configured to change which of the end node and access point the first and second radios and the first and second processors are configured to communicate with.

Aspects include A network range extender a first radio to wirelessly communicate with an access point, a first antenna element coupled to a radio frequency (rf) input and output of the first radio, a first processing device programmed to control and process messages received from the first radio, a second radio to wirelessly communicate with an end node, a second antenna element coupled to a radio frequency (rf) input and output of the second radio, and a second processing device programmed to control and process messages received from the second radio.

Aspects also include a networked detection system including a network of sensors, a gateway to provide a network connection to connect the one or more sensor devices to the network, and a range extender for connecting the one or more sensor devices to the gateway, with the range extender a first radio to wirelessly communicate with the access point, a first processing device programmed to control and process messages received from the first radio, a second radio to wirelessly communicate with the end node, and a second processing device programmed to control and process messages received from the second radio.

One or more advantages may be provided by the one or more aspects.

The architecture has multiple radios manage a radio frequency (RF) band where the radios may coordinate operation. For example, a radio can contact (e.g., ping) a communication channel and thereafter begin communicating with an end node over that channel. That radio/processor may inform any other radios on that side of the range extender that it is active in a frequency band, which can cause the other radios to alter their channel scanning processes. The range extender is able to support varied protocols to end nodes, while providing a single interface to an access point connected to a gateway. The available radio processor combinations allow monitoring of end node operation. In some implementations, an access point may operate as a translator and provide a proxy for access point protocols.

The details of one or more embodiments of the invention are set forth in the accompanying drawings and the description below. Other features, objects, and advantages of the invention is apparent from the description and drawings, and from the claims.

DETAILED DESCRIPTION

Described herein are examples of network features that may be used in various contexts including, but not limited to, security/intrusion and alarm systems. Example security systems may include an intrusion detection panel that is electrically or wirelessly connected to a variety of sensors. Those sensors types may include motion detectors, cameras, and proximity sensors (used, e.g., to determine whether a door or window has been opened). Typically, such systems receive a relatively simple signal (electrically open or closed) from one or more of these sensors to indicate that a particular condition being monitored has changed or become unsecure.

For example, typical intrusion systems can be set-up to monitor entry doors in a building. When a door is secured, a proximity sensor senses a magnetic contact and produces an electrically closed circuit. When the door is opened, the proximity sensor opens the circuit, and sends a signal to the panel indicating that an alarm condition has occurred (e.g., an opened entry door).

Data collection systems are becoming more common in some applications, such as home safety monitoring. Data collection systems employ wireless sensor networks and wireless devices, and may include remote server-based monitoring and report generation. As described in more detail below, wireless sensor networks generally use a combination of wired and wireless links between computing devices, with wireless links usually used for the lowest level connections (e.g., end-node device to hub/gateway). In an example network, the edge (wirelessly-connected) tier of the network is comprised of resource-constrained devices with specific functions. These devices may have a small-to-moderate amount of processing power and memory, and may be battery powered, thus requiring that they conserve energy by spending much of their time in sleep mode. A typical model is one where the edge devices generally form a single wireless network in which each end-node communicates directly with its parent node in a hub-and-spoke-style architecture. The parent node may be, e.g., an access point on a gateway or a sub-coordinator which is, in turn, connected to the access point or another sub-coordinator.

Figure 1:
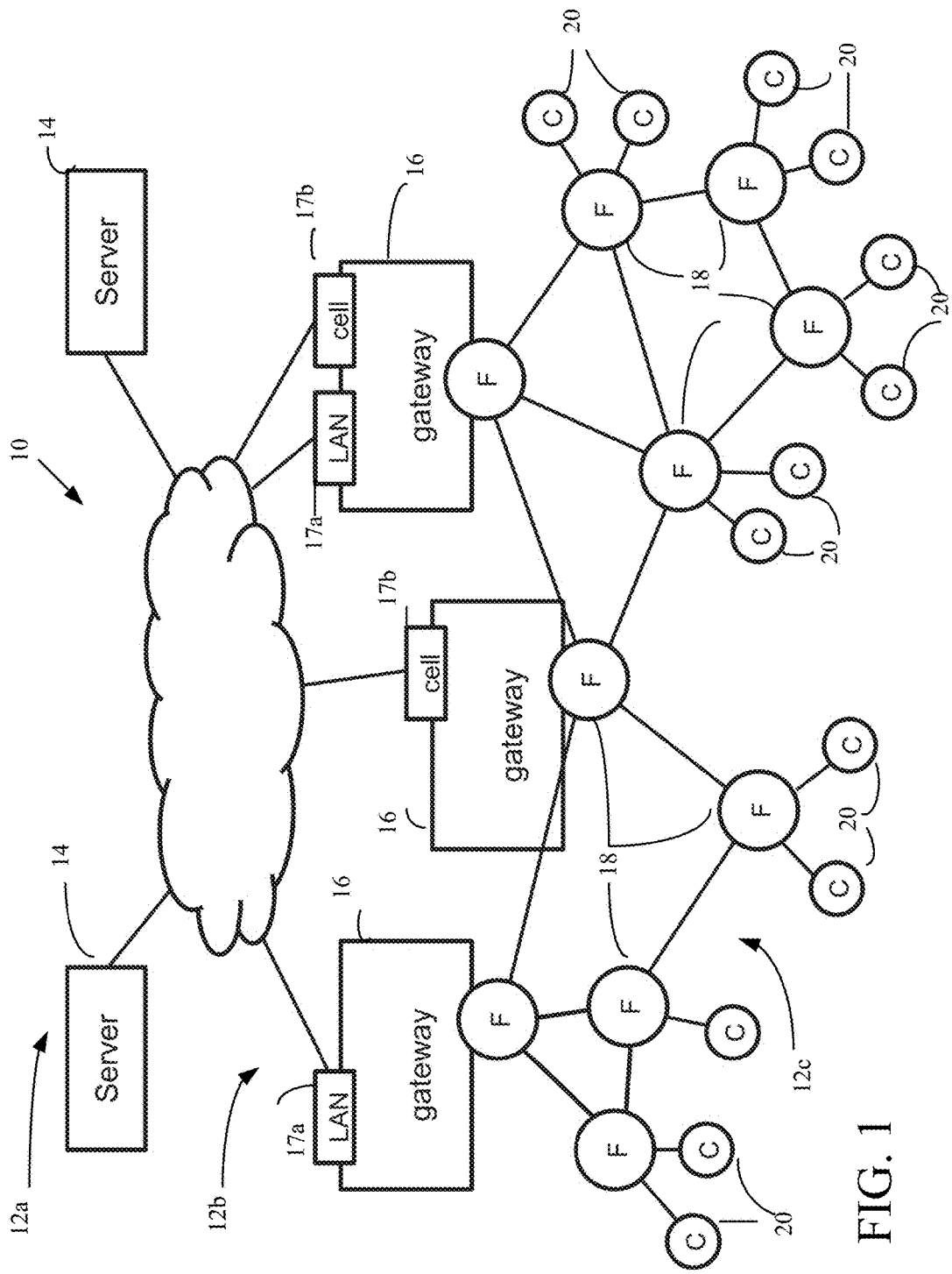
FIG. 1 is a schematic diagram of an exemplary networked security system.

Referring now to FIG. 1, an exemplary (global) distributed network 10 topology for a Wireless Sensor Network (WSN) is shown. In FIG. 1 the distributed network 10 is logically divided into a set of tiers or hierarchical levels 12a-12c.

In an upper tier or hierarchical level 12a of the network are disposed servers and/or virtual servers 14 running a "cloud computing" paradigm that are networked together using well-established networking technology such as Internet protocols or which can be private networks that use none or part of the Internet. Applications that run on those servers 14 communicate using various protocols such as for Web Internet networks XML/SOAP, RESTful web service, and other application layer technologies such as HTTP and ATOM. The distributed network 10 has direct links between devices nodes) as shown and discussed below.

The distributed network 10 includes a second logically divided tier or hierarchical level 12b, referred to here as a middle tier that involves gateways 16 located at central, convenient places inside individual buildings and structures. These gateways 16 communicate with servers 14 in the upper tier whether the servers are stand-alone dedicated servers and/or cloud based servers running cloud applications using web programming techniques. The middle tier gateways 16 are also shown with both local area network 17a (e.g., Ethernet or 802.11) and cellular network interfaces 17b.

The distributed network topology also includes a lower tier (edge layer) 12c set of devices that involve fully-functional sensor nodes 18 (e.g., sensor nodes that include wireless devices, e.g., transceivers or at least transmitters, which in FIG. 1 are marked in with an "F") as well as constrained wireless sensor nodes or sensor end-nodes 20 (marked in the FIG. 1 with "C"). In some embodiments wired sensors (not shown) can be included in aspects of the distributed network 10.

Constrained computing devices 20 as used herein are devices with substantially less persistent and volatile memory other computing devices, sensors in a detection system. Currently examples of constrained devices would be those with less than about a megabyte of flash/persistent memory, and less than 10-20 kbytes of RAM/volatile memory). These constrained devices 20 are configured in this manner; generally due to cost/physical configuration considerations.

In a typical network, the edge (wirelessly-connected) tier of the network is comprised of highly resource-constrained devices with specific functions. These devices have a small-to-moderate amount of processing power and memory, and often are battery powered, thus requiring that they conserve energy by spending much of their time in sleep mode. A typical model is one where the edge devices generally form a single wireless network in which each end-node communicates directly with its parent node in a hub-and-spoke-style architecture. The parent node may be, e.g., an access point on a gateway or a sub-coordinator which is, in turn, connected to the access point or another sub-coordinator.

Each gateway is equipped with an access point (fully functional node or "F" node) that is physically attached to that access point and that provides a wireless connection point to other nodes in the wireless network. The links (illustrated by lines not numbered) shown in FIG. 1 represent direct (single-hop network layer) connections between devices. A formal networking layer (that functions in each of the three tiers shown in FIG. 1) uses a series of these direct links together with routing devices to send messages (fragmented or non-fragmented) from one device to another over the network.

The WSN 10 implements a state machine approach to an application layer that runs on the lower tier devices 18 and 20. Discussed below is an example of a particular implementation of such an approach. States in the state machine are comprised of sets of functions that execute in coordination, and these functions can be individually deleted or substituted or added to in order to alter the states in the state machine of a particular lower tier device.

The WSN state function based application layer uses an edge device operating system (not shown, but such as disclosed in the above mentioned provisional application) that allows for loading and execution of individual functions (after the booting of the device) without rebooting the device (so-called "dynamic programming"). In other implementations, edge devices could use other operating systems provided such systems allow for loading and execution of individual functions (after the booting of the device) preferable without rebooting of the edge devices.

Described below is a network range extender with multi RF radio support. Range extenders have been implemented as repeaters or sub-coordinators in mesh networks. Accordingly, in this description the term "range extender" includes, but is not limited to repeaters and coordinators/sub-coordinators in a mesh network. A mesh network may be implemented by various range extenders that form a self-healing network. A self-healing network re-routes network paths if a path to a network node is interrupted. Low-power networks and sensor networks (FIG. 1) can use range extenders having one radio and one processor. Such a standard range extender may multiplex wireless communications to access points and end nodes of the network that the range extender services.

That is, the range extender includes a single radio that is managed by a single processor and that is programmed to time multiplex its operation to support two interfaces—one to the end node and one to the access point. This support includes, but is not limited to, frequency agility/hopping and selection, protocol management and control, message storage and forwarding, as well as, managing protocol state and environmental functions. An example of an end node is a sensor device that is a termination point on a network. An example of an access point is a base station or the like, through which other devices may communicate on the network.

In some cases, networks use processors that are constrained in performance and memory in order to achieve low cost. These processors may be significantly constrained compared to the type of processors used in cell phones and other communication devices. Low-power/low energy networks can also include battery-operated or energy-harvesting devices that sleep (e.g., enter a low power state) for periods of time. Managing multiple wireless interfaces and RF protocols can consume available processor bandwidth and memory from a single-processor-range-extender technology. Also, network operations may be slowed by having to multiplex and manage two wireless interfaces. Performance also may suffer as one side of the interface has to wait for the other side to complete its operation.

Architectures having multiple processors and multiple radios have been used to implement protocol translation and frequency and protocol conversion, and to expand a local area network (LAN) into a wide area network (WAN) (e.g., cell modems for WAN). The approaches described below enable operation on a same frequency band and use of a same standard protocol, such as IEEE 802.15.4 and are implemented in a range extender that includes on each of its end node side and access point side one or more radios and one or more processors corresponding to each radio for each side. The range extender may be part of a network having power sensitive devices including, hut not limited to, devices that perform battery harvesting or energy harvesting.

The example hardware architecture described herein may allow software processes to leverage the flexibility of the hardware (multiple radios and processors) to enable operation with constrained end node devices. In general, software processes, such as those used for sensor networks, can be analogues to a Global System for Mobile communications (GSM) cell modem architecture, where a plurality of control channels are used and mobile devices are managed and dedicated for operation from an idle state through the user of control channels. The concept of a plurality of control channels and allocation of communication channels for mobile device communication may also be applied to these low-power sensor networks.

In this regard, in a traditional approach, an end node may go to a channel and wait for a controlling source to service that channel. Alternatively, the end node may go to one of the control channels and then wait for the availability of the control source to service the control channel or channels. The control source announces which channel will be active next on the command channels. This can result in a delay while the node listens on the control channel. Furthermore, one or more devices can wake-up and need to be serviced. All such devices would go to one of the control channels, but the more control channels there are, the longer it takes to reach the listening node. Also, the devices listening on the control channel will go to the next communication channel, which may result collisions if multiple devices attempt access at the same time.

In the case of a single-radio/processor range extender, the end node may need to wait until the processor completes its present operation and goes to one of the control channels to announce which communication channel will be used, similar to a GSM cell modem. The 802.15.4 physical (THY) layer allows a maximum 127 bytes per packet, including payload.

Figures 1A, 1B:
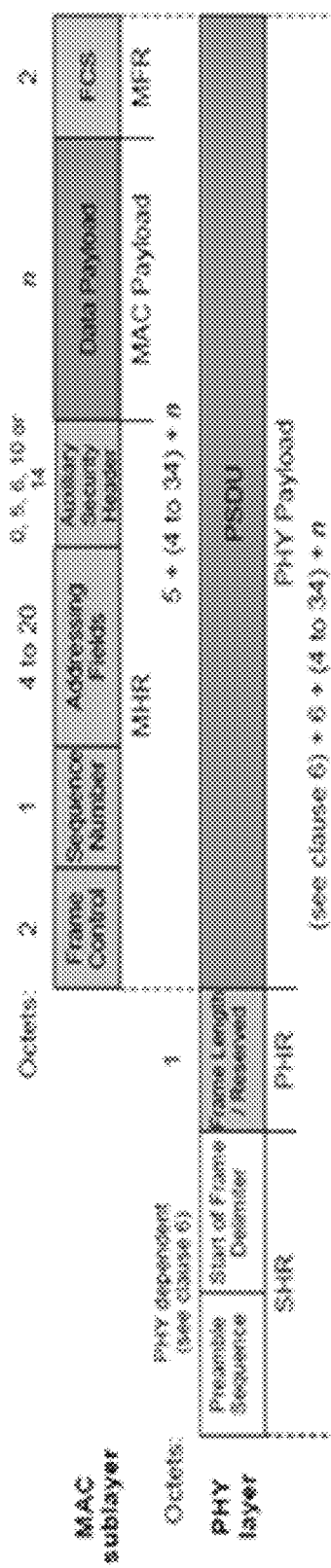
FIGS. 1A and 1B show exemplary data frame and PHY packet and 6LoWPAN mesh type and header respectively.

Referring now to FIG. 1A, an example of an 802.15.4 packet is shown. A 802.15.4 packet refers to IEEE standard 802.15.4, which specifies the physical layer and media access control for low-rate wireless personal area networks (LR-WPANs). The standard is maintained by the IEEE 802.15 working group. The packet contains an address field used for point to point transfer of a message. An 802.15.4 packet with 6LoWPAN (low power IPv6 working group), UDP (User Datagram Protocol) and other protocols transmit approximately 100 bytes or less in a packet. A packet is larger than 127 bytes if the radio frequency (RE) requirements of preamble and sync are included. For 100 bytes at 250 KHz with 27 bytes of overhead, approximately 0.5 milliseconds is used in transmission. Turnaround time to send an acknowledge packet and to process information adds additional time. Approximately a millisecond therefore may be used in a communication cycle with an end node. A transmission of a few bytes may take less time, estimating about 0.7 ms. since processing overhead and message acknowledge (ack) is still present.

Typically, a dwell time is used to service multiple devices. Atypical dwell time on a communication channel can be 10 ms or more, thus an end node listening on a control channel may wait 10 ms or longer for service. The wait increases if multiple announcements are made in multiple control channels. After communicating on a channel, the access point or range extender may announce its next communication channel in different ways. However, time is spent frequency hopping and announcing the next communication channel.

Referring now to FIG. 1B, an example of a 6LoWPAN mesh type header is shown. The same operation occurs, as the end node sends a message to the access point. For example, a range extender receives a message from the access point and uses its routing protocol and routing table to forward the message to the next node along a path to its final destination, the end node. From range extender routing table, the range extender may use the final destination, next hop location (for that destination), and the number of estimated hops in order to reach the final destination. If the final destination and the next hop location are the same, the estimated number of hops is zero and the end node is reached.

The processes described herein define a multi-radio architecture suited for power sensitive devices powered from battery or an energy harvesting element. In some implementations only the payload and routing information is sent from the access point side to the scanning radios on the end node side of the range extender. Each side of the range extender can operate independently, even with different PHY protocols or frequency of operation. In some implementations, a single radio can only communicate with a single device at a time. For a single RF channel, if more than one device seeks to communicate with an access point, the devices may have to take turns.

Protocol challenges may occur when servicing both sides of a wireless network using a single radio and has to schedule message transfers or managing nodes that wake-up as in a low cost/low power wireless network. In addition to the network functions already described, a range extender or access point may need to maintain synchronization with a corresponding access point.

Described is a split architecture in which independent radios interface to each side of the wireless network and one or more processors control a corresponding radio or radios. Example implementations may include the use of digital modulation that allows a network to manage its channel plan by not requiring frequency hopping or the use of a pre-defined number of channels. Digital modulation as discussed below can be used to manage channel usage and respond to nodes that wake-up.

In some cases, the processes described herein may improve the speed of identification of sleeping devices that wake to transmit or listen for information. In some networks, the access point only communicates with the range extender or with an end node. When a node is associated with a range extender and the range extender is associated with an access point, in order for the access point to reach the end node, the access point sends its message to the range extender, and the range extender uses a routing protocol to send the message to the end node. The information on where the access point message is to be sent next by the range extender (hop) is determined by the information in the 6LoWPAN payload.

Figure 2:
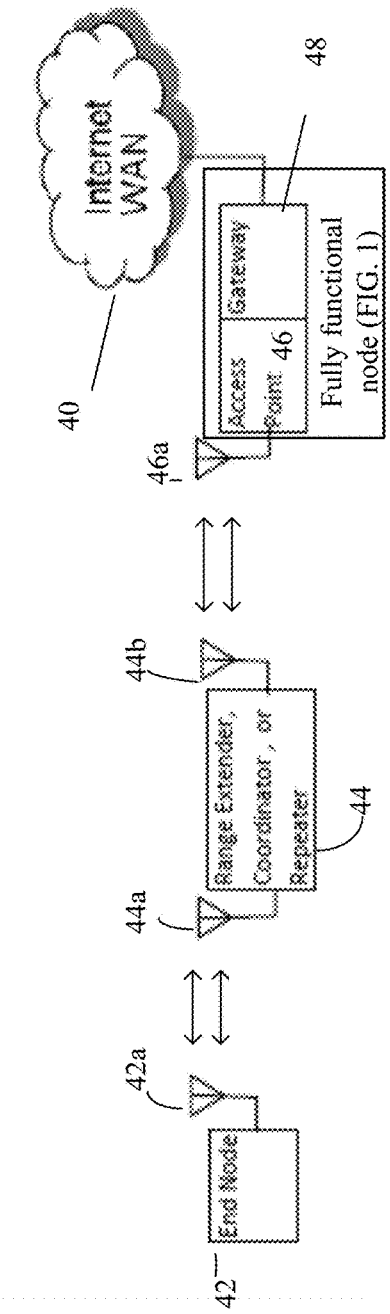
FIG. 2 is a block diagram of a network, which can be the network of FIG. 1 and which includes an exemplary range extender having a first radio and processor for communicating with an end node and a second radio and processor for communicating with an access point.

Referring now to FIG. 2, an example architecture 40 including a network 41 having an end node, range extender and access point is shown. The network can be any network that includes wireless end nodes and in particular can be the WSN network 10 shown in FIG. 1. In general, the network 40 includes plural end nodes (one end node 42 is shown in FIG. 2), one or more range extenders (one range extender 44 is shown in FIG. 2), and one or more access points (one access point 46 is shown in FIG. 2). Each of the end nodes, e.g., end node 42 and access points, e.g., access point 46 include corresponding antennas 42a, 46a for transmission/reception of signals. Each of the range extenders, e.g., range extender 44, also includes a pair of antennas 44a, 44b for transmission/reception of signals between the end nodes 42 and access points 46 respectively. Thus, in FIG. 2, end node 42 transmits/receives signals via antennas 42a and 44a and access point 46 receives/transmits signals via antennas 44b and 46a. The access point 46 is coupled to a gateway 48 that couples to the network 40.

Figure 3:
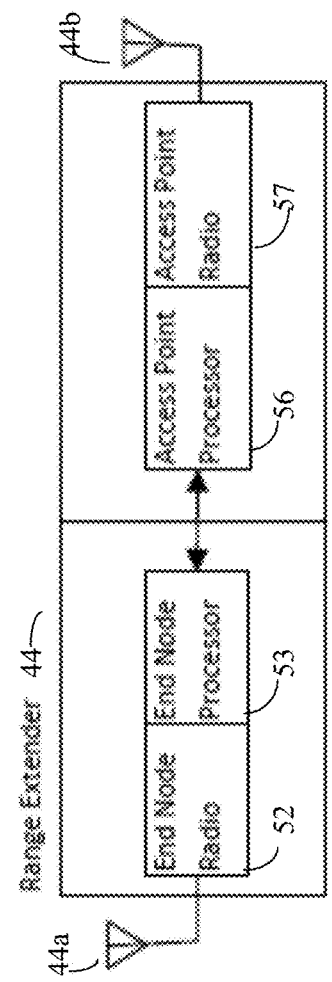
FIG. 3 is a block diagram of an example range extender having a first radio and processor for communicating with an end node and a second radio and processor for communicating with an access point.

Referring now to FIG. 3, an example range extender 44 includes an end node radio 52 and an end node processor 53 for communicating with the end node 42 (FIG. 2) and an access point radio 57 and an access point processor 56 for separately communicating with the access point 46 (FIG. 2). The processors 53, 56 control respective radios 52, 57. The processors 53, 56 engage in a process for communicating between processors 53, 56, in which wireless messages from one side of the network (e.g., the access point side) are recovered and processed by processor 56 and transferred to the processor 53 on the other side of the network (e.g., the end node side). Message transfers can take place using direct memory access (DMA) or other transfer methods between processors 53, 56. Each processor 53, 56 manages its own wireless communication on the side of the wireless interface (the access point or the end node) to which it is connected. Processor support includes, but is not limited to, frequency agility/hopping and selection, protocol management and control, message store and forward, as well as, managing protocol state and environmental functions.

The processors 53, 56 on different sides of the network (e.g., the end node side and the access point side) may also exchange any appropriate tuning parameters, which may, in some implementations, improve network performance. This can include, but is not limited to, frequency usage in maintaining orthogonal frequency transmissions, communicating with an end node, and other operating conditions, such as, statistics that communicate the health and status of operations.

In other implementations of range extender 44 there may be more than one end node radio and/or more than one end node processor for communicating with the end node or end nodes, and more than one access point radio and/or more than one access point processor for separately communicating with the access point or access points.

In range extender 44, the distinctiveness of each side of the network, and how it is divided in the range extender 44, allows for tracking of the interface to the access point, as well as, tracking of the end node. The range extender 44 removes the risk of missing an access point message because the range extender 44 is managing the other side of the network and vice a versa.

While, in FIG. 3, separate end node and access point processors 53 and 56 are used, in some implementations a single multi-core processor may be used with one or more cores dedicated to operations associated with the end node 42 and one or more, different cores dedicated operations associated with to the access point 46. It is also feasible for the range extender 44 to support multiple wireless protocols in a single frequency band. This may be done by having each separate processor 53, 56 manage a protocol and radio interface. Also, a higher-performance multi-core processor could be used to manage multiple radios on a single side.

Range extenders used in a constrained network, e.g., a network comprising constrained device, as discussed in FIG. 1, there is one radio that multiplexes information from the access point and the same radio re-transmits information to end node. This approach however requires the use of synchronization processes (e.g., precise timers and end of operations on each side of the network), and may affect the rate at which information transfer occurs. The range extender 44 of FIG. 3 decouples operation between the two sides, namely the end node and access point sides, so that there is no need to multiplex network communications using a single radio. Channel usage and other parameters are managed so that both radios are not operating on the same channel simultaneously.

For North American operation, an example implementation uses wide modulation occupying a 6 dB bandwidth of 500 KHz. The FCC allows single channel operation for wide digital modulation. This modulation bandwidth can be obtained in various ways, even if the data rate itself is not 250 KHz. This modulation allows a radio 52 to stay on one channel and communicate with an end node 42. A different radio 57 may communicate in a different channel simultaneously with an access point 46. Data transmitted digitally over an RF channel is called digital modulation. An RF frequency used by a radio is referred to herein as a channel. The frequency is affected in some way by the data being transmitted. Examples of modulation techniques that are typically used in communications include amplitude modulation (AM), on-off keying (OOK), frequency-shift keying (FSK), phase-shift keying (PSK), and Quadrature amplitude modulation (QAM). Other modulation techniques could be used. Generally, the frequency spectrum generated by modulation of a frequency is characterized by the characteristics of the modulation.

Figure 4:
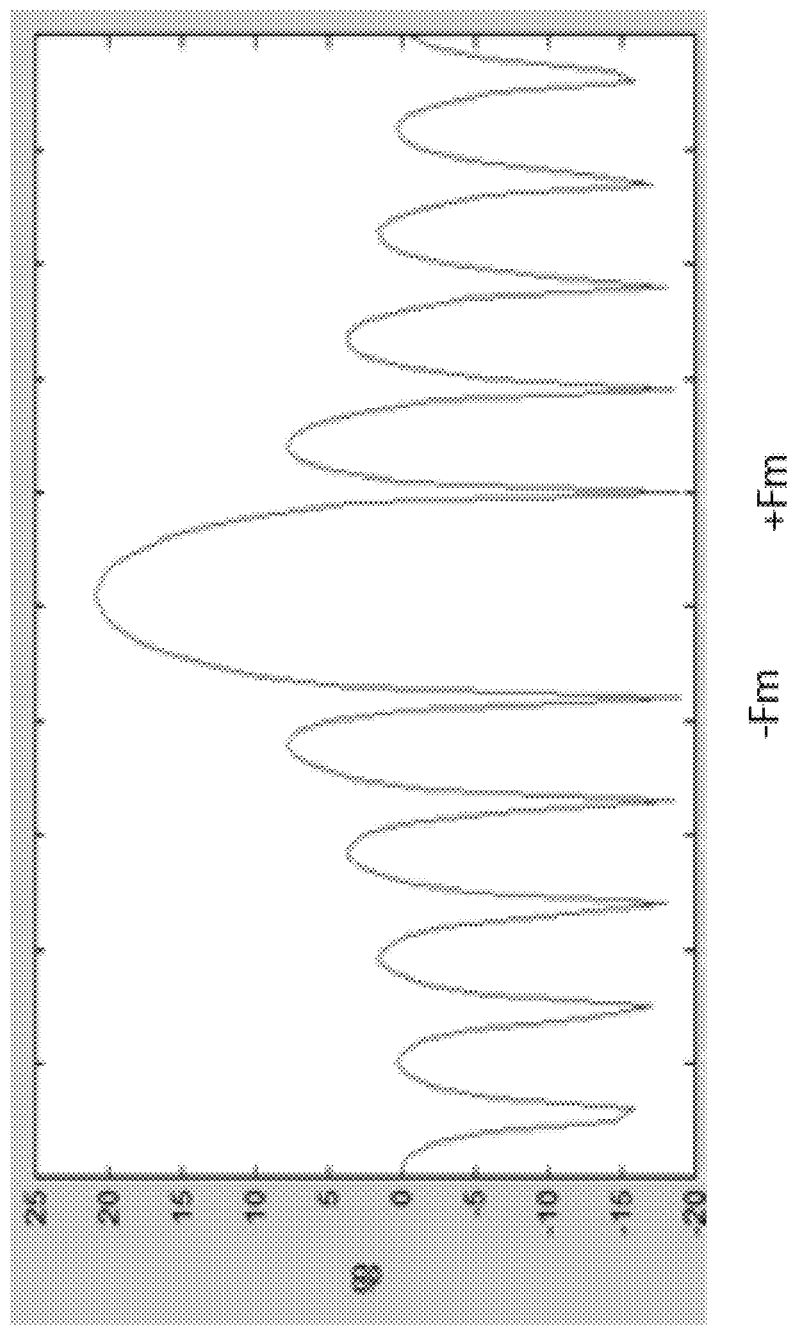
FIG. 4 is a graph showing an example of a frequency spectrum generated by modulation.

Referring to FIG. 4, if the modulating signal is 250 KHz and modulation is OOK, PSK or a similar modulation technique, the frequency spectrum will have the main lobes occupy a 500 KHz band as shown.

Figure 5:
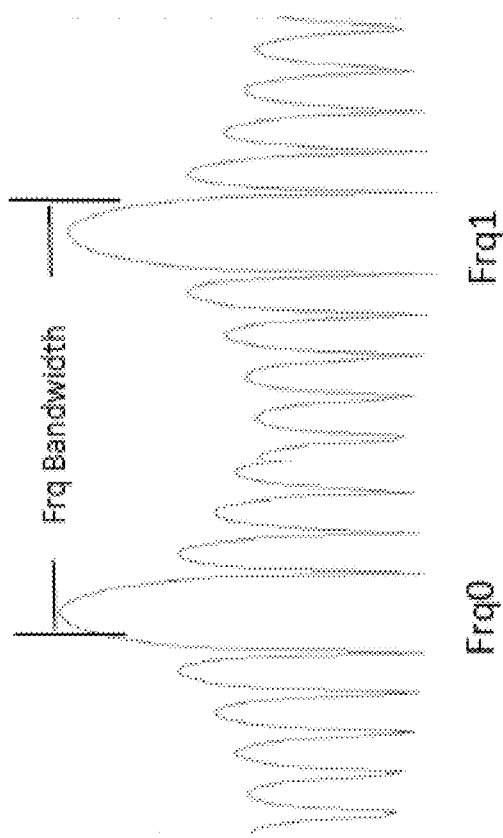
FIG. 5 is a graph showing an example of frequency bandwidth.

Referring to FIG. 5, digital modulation occupying the 500 KHz 6 dB bandwidth can also be produced with FSK modulation, as shown. FSK modulation uses two frequencies to represent a one or a zero. The difference in frequency defines the occupied bandwidth. The actual modulation rate defines the lobes as described above. The implementations described herein are examples, and there may be many different types of implementations.

Figure 6:
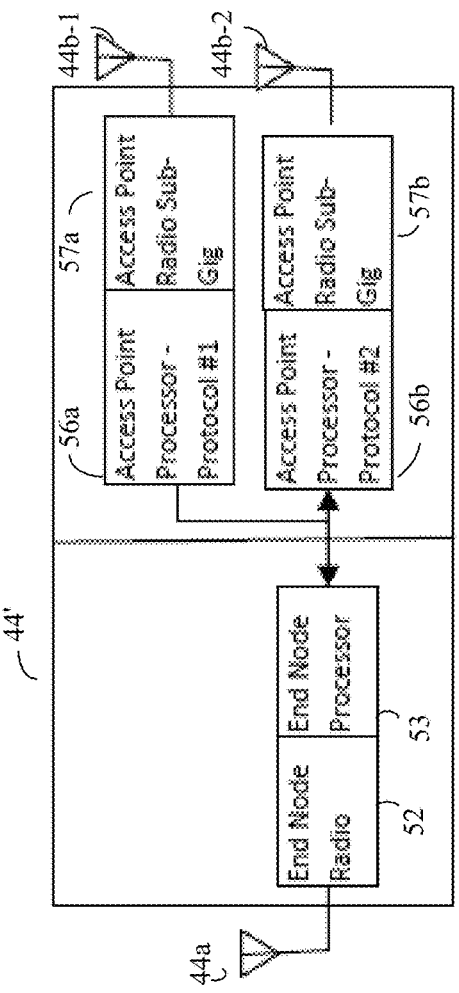
FIG. 6 is a block diagram of an example range extender having radios and processors for a plurality of communication channels used by the range extender to plural access points.

Referring now to FIG. 6, an access point processor 56a, 56b and an access point radio 57a, 57b are provided along with antenna 44b-1 and 44b-2 for each channel used by the range extender 44' and access point (not shown). The radios 57a, 57b listen for any node that wakes-up on any channel. A node may wake-up and transmit immediately to the range extender 44'. Alternatively, the range extender 44' may send continuous pings and a node may responds when the node wakes-up. For a network with a relatively low number of channels, this approach may be used.

In alternative implementations, one or more processors can manage a number of radios to the access point or to the end node. In some implementations, channels can be allocated based on the need for fast network acquisition. For example, in the range extender 44 of FIG. 2, one or more radios are dedicated to listen on particular channels for nodes that are power sensitive (battery or harvesting), whereas, main-line powered end nodes would operate using a different channel allocation. The channels are interleaved between energy sensitive and main-line power or split between a high and low band manner. More channels may be allocated to one type of node. An advantage of this type of architecture is that main-line power devices would not tie-up a radio and starve (from access) an energy sensitive end node, as may occur in a single processor architecture.

Figure 7:
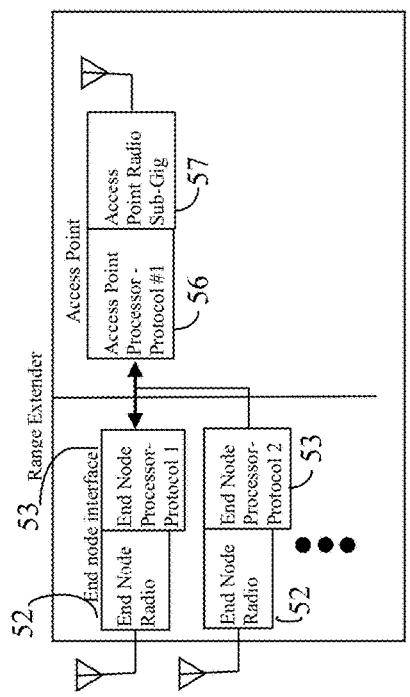
FIG. 7 is a block diagram of an example range extender having radios and processors for a plurality of communication channels used by the range extender to plural end nodes.

Referring to FIG. 7, two or more radios (generally 52) with processors (generally 53) and antennas (not referenced) can be dedicated to manage energy sensitive node channels, with a single access point processor 56 and access point radio 57(and antenna), as shown. With two radios 52 available, one of the two radios can randomly or periodically service the main power channels, allowing the energy sensitive node to be serviced more frequently. By allocating more radios 52 to energy sensitive end node channels, random channel selection by an end node may allow for improved communication by reducing collisions. As was the case above, a radio per channel may be used for power sensitive devices and for mains power devices or radios can be shared among multiple channels.

The use of multiple radios 52 can be used in different processes. For example if three radios not shown) are available for a range extender, each radio can be controlled by its corresponding processor to change its prescribed functionality based on network measurements, settings, or other criteria. For example, if one of the radios is communicating with the access point that radio could be configured by its corresponding processor to change to scanning the end node side. Thus, the radio's function can be changed from access point communications to end node side communications.

Figure 8:
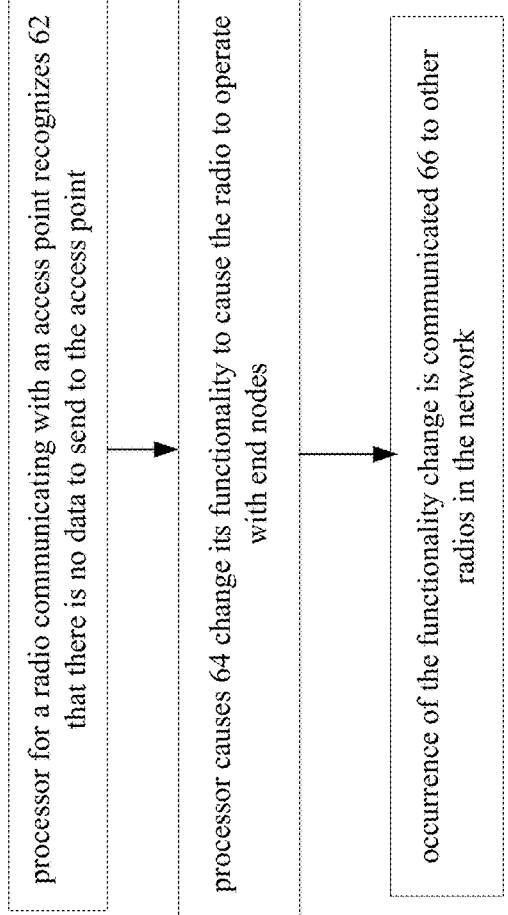
FIG. 8 is a flow chart of an example range extender process having radios and processors for a plurality of communication channels used by the range extender to plural end nodes.

Referring now to FIG. 8, in an example process 60 where a processor/radio changes functionality, the following operations are performed. The processor 57 for a radio 56 communicating with an access point; recognizes 62 that there is no data to send to the access point. In the next frequency change, the processor causes 64 the radio to change its functionality to operate on the end node side.

The occurrence of the functionality change is communicated 66 to other radios in the network. This communication includes in addition to the change, an expected dwell time that the access point will use at the next frequency. Before the end of the dwell time, one of the radios may change its personality to communicate on the access node side.

Which radio/processor changes its personality may depend on which radio/processor did not find an end node when scanning. Alternatively, a radio completing an operation on a main-line power channel may not initiate another transfer and its corresponding processor may change the radio's functionality if the processor associated with that radio sees that the other radios are busy and the dwell time will soon expire.

If all channels are energy sensitive, one of the radios completing receipt of a wireless packet may inform the other radios on the network that a packet is available for processing and which channel is being used. The radio/processor may change functionality to access point communication.

During a period of time, and in a case where there is more than one (e.g., three) processors on an end node side, all processors may be active on the end node side. A benefit of having multiple radios is that if an end node finds that a channel is busy, the end node may change to another channel, which would have a corresponding radio (radio per channel for energy sensitive nodes). This reduces the time that an end node has to wait to communicate with the range extender.

Advantages of the processes described herein may be particularly applicable to, although not limited to, a network, such as an 802.15.4, network. For example, a range extender can implement the architecture of FIG, 3 and, as such, may be able to respond, in real time, to events on both sides of the wireless interface (the end node and access point side). Tracking frequency hopping on each side of the network may be enabled, in some implementations, because messages from the access point are not missed due to servicing the end node side of the interface. Also, the end node side of the range extender can issue messages and listen for steeping nodes that wake-up. Digital modulation may be used in order to meet single channel operation and develop a channel plan with multiple radios.

Figure 9:
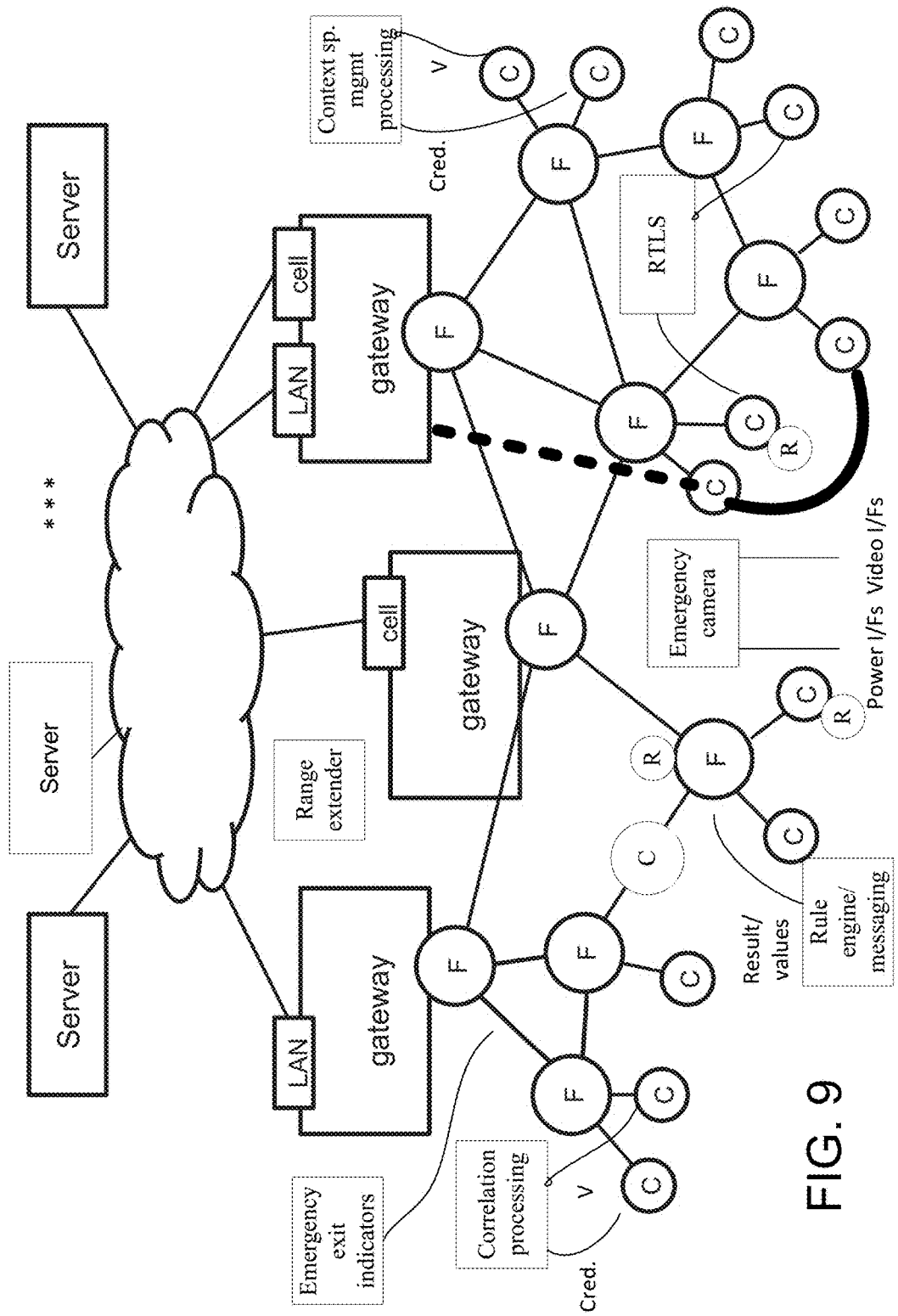
FIG. 9 is a block diagram of components of an example networked security system.

FIG. 9 shows an example of a security system having features of the WSN described with respect to FIG. 1 and having the various functionalities described herein. As shown in FIG. 9, correlation processing receives inputs from certain constrained nodes (although these can also be fully functional nodes). These inputs may include credential information and video information, and the correlation processing may produce correlated results that are sent over the network. Context management processing receives inputs from certain constrained nodes (although these can also be fully functional nodes) e.g., credential information and video and grouping information, and performs context processing with results sent over the network. The network supports operation of emergency exit indicators; emergency cameras as welt as distributed rule processing and rule engine/messaging processing. Range extenders are used with e.g., gateways, and a real time location system receives inputs from various sensors (e.g., constrained type) as shown. Servers interface to the WSN via a cloud computing configuration and parts of some networks can be run as sub-nets.

The sensors provide in addition to an indication that something is detected in an area within the range of the sensors, detailed additional information that can be used to evaluate what that indication may be without the intrusion detection panel being required to perform extensive analysis of inputs to the particular sensor.

For example, a motion detector could be configured to analyze the heat signature of a warm body moving in a room to determine if the body is that of a human or a pet. Results of that analysis would be a message or data that conveys information about the body detected. Various sensors thus are used to sense sound, motion, vibration, pressure, heat, images, and so forth, in an appropriate combination to detect a true or verified alarm condition at the intrusion detection panel.

Recognition software can be used to discriminate between objects that are a human and objects that are an animal; further facial recognition software can be built into video cameras and used to verify that the perimeter intrusion was the result of a recognized, authorized individual. Such video cameras would comprise a processor and memory and the recognition software to process inputs (captured images) by the camera and produce the metadata to convey information regarding recognition or lack of recognition of an individual captured by the video camera. The processing could also alternatively or in addition include information regarding characteristic of the individual in the area captured/monitored by the video camera. Thus, depending on the circumstances, the information would be either metadata received from enhanced motion detectors and video cameras that performed enhanced analysis on inputs to the sensor that gives characteristics of the perimeter intrusion or a metadata resulting from very complex processing that seeks to establish recognition of the object.

Sensor devices can integrate multiple sensors to generate more complex outputs on that the intrusion detection panel can utilize its processing capabilities to execute algorithms that analyze the environment by building virtual images or signatures of the environment to make an intelligent decision about the validity of a breach.

Memory stores program instructions and data used by the processor of the intrusion detection panel. The memory may be a suitable combination of random access memory, and read-only memory, and may host suitable program instructions (e.g. firmware or operating software), and configuration and operating data and may be organized as a file system or otherwise. The stored program instruction may include one or more authentication processes for authenticating one or more users. The program instructions stored in the memory of the panel may further store software components allowing network communications and establishment of connections to the data network. The software components may, for example, include an internet protocol (IP) stack, as well as driver components for the various interfaces, including the interfaces and the keypad. Other software components suitable for establishing a connection and communicating across network will be apparent to those of ordinary skill.

Program instructions stored in the memory, along with configuration data may control overall operation of the panel.

The monitoring server includes one or more processing devices (e.g., microprocessors), a network interface and a memory (all not illustrated). The monitoring server may physically take the form of a rack mounted card and may be in communication with one or more operator terminals (not shown). An example monitoring server is a SURGARD™ SG-System Virtual, or similar system.

The processor of each monitoring server acts as a controller for each monitoring server, and is in communication with, and controls overall operation, of each server. The processor may include, or be in communication with, the memory that stores processor executable instructions controlling the overall operation of the monitoring server. Suitable software enable each monitoring server to receive alarms and cause appropriate actions to occur. Software may include a suitable :Internet protocol (IP) stack and applications/clients.

Each monitoring server of the central monitoring station may be associated with an IP address and port(s) by which it communicates with the control panels and/or the user devices to handle alarm events, etc. The monitoring server address may be static, and thus always identify a particular one of monitoring server to the intrusion detection panels. Alternatively, dynamic addresses could be used, and associated with static domain names, resolved through a domain name service.

The network interface card interfaces with the network to receive incoming signals, and may for example take the form of an Ethernet network interface card (NIC). The servers may be computers, thin-clients, or the like, to which received data representative of an alarm event is passed for handling by human operators. The monitoring station may further include, or have access to, a subscriber database that includes a database under control of a database engine. The database may contain entries corresponding to the various subscriber devices/processes to panels like the panel that are serviced by the monitoring station.

All or part of the processes described herein and their various modifications (hereinafter referred to as "the processes") can be implemented, at least in part, via a computer program product, i.e., a computer program tangibly embodied in one or more tangible, physical hardware storage devices that are computer and/or machine-readable storage devices for execution by, or to control the operation of, data processing apparatus, e.g., a programmable processor, a computer, or multiple computers. A computer program can be written in any form of programming language, including compiled or interpreted languages, and it can be deployed in any form, including as a stand-atone program or as a module, component, subroutine, or other unit suitable for use in a computing environment. A computer program can be deployed to be executed on one computer or on multiple computers at one site or distributed across multiple sites and interconnected by a network.

Actions associated with implementing the processes can be performed by one or more programmable processors executing one or more computer programs to perform the functions of the calibration process. All or part of the processes can be implemented as, special purpose logic circuitry, e.g., an FPGA (field programmable gate array) and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, e.g., magnetic, magneto-optical disks, or optical disks.

Tangible, physical hardware storage devices that are suitable for embodying computer program instructions and data include all forms of non-volatile storage, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks and volatile computer memory, e.g., RAM such as static and dynamic RAM, as well as erasable memory, e.g., flash memory.

In addition, the logic flows depicted in the figures do not require the particular order shown, or sequential order, to achieve desirable results. In addition, other actions may be provided, or actions may be eliminated, from the described flows, and other components may be added to, or removed from, the described systems. Likewise, actions depicted in the figures may be performed by different entities or consolidated.

Elements of different embodiments described herein may be combined to form other embodiments not specifically set forth above. Elements may be left out of the processes, computer programs, Web pages, etc. described herein without adversely affecting their operation. Furthermore, various separate elements may be combined into one or more individual elements to perform the functions described herein.

Other implementations not specifically described herein are also within the scope of the following claims.

What is claimed is:

1. An apparatus for use in a network that comprises an access point and an end node, the apparatus comprising:
   a first radio to wirelessly communicate with the access point;
   a second radio to wirelessly communicate with the end node;
   a first processor device programmed to control and process messages received from the first radio, the first processing device configured to determine whether the first radio is required to send data to the access point;
   a second processor device programmed to control and process messages received from the second radio, the second processing device configured to determine whether the second radio is required to send data to the end node; and
   wherein when either one of the first or second processor devices determines that respective radios are not required to send data, the determined one of the first or the second processor devices is configured to change which of the end node and the access point, the first and second radios and the first and second devices are configured to communicate with.

2. The apparatus of claim 1, wherein the first processor device changes which of the end node and the access point to communicate with by determining that there are no data to send to the access point, and in a next frequency change, the first processor device causes the first radio to change its functionality to communicate with the end node.

3. The apparatus of claim 2, wherein the occurrence of the functionality change is communicated to other radios in the network with a communication including an expected dwell time that the access point will use at the next frequency.

4. The apparatus of claim 1, wherein at least one of the first radio and the second radio is controllable to listen on one or more communication channels for devices having at least one predefined power characteristic.

5. The apparatus of claim 1, wherein the first and second processor devices exchange communications between the processor devices using direct memory access (DMA) transfers between the processor devices.

6. The apparatus of claim 1, wherein the first and second processor devices each manages its own wireless communication on the side of the apparatus to which the respective processor device is connected.

7. The apparatus of claim 1, wherein the first and second processor devices each provide frequency agility/hopping and selection, protocol management and control, message store and forward services and manage protocol state and environmental functions for the respective radio.

8. The apparatus of claim 1, wherein the first processor device is provided by one or more cores of a multicore processor and the second processor device is provided by one or more different cores of the multicore processor.

9. The apparatus of claim 1, wherein the apparatus is a range extender.

10. The apparatus of claim 1, wherein the first radio is part of a set of a plurality of first radios that service a corresponding plurality of access points.

11. The apparatus of claim 1, wherein the second radio is part of a set of a plurality of second radios that service a corresponding plurality of end nodes.

12. An apparatus comprising:
   a first radio to wirelessly communicate with an access point;
   a second radio to wirelessly communicate with an end node;
   a first antenna element coupled to a radio frequency (r.f.) input and output of the first radio;
   a first processor device programmed to control and process messages received from the first radio, the first processor device configured to determine whether the first radio is required to send data to the access point;
   a second antenna element coupled to a radio frequency (r.f.) input and output of the second radio; and
   a second processor device programmed to control and process messages received from the second radio, the second processor device configured to determine whether the second radio is required to send data to the end node
   wherein the apparatus is a range extender and when either of the first and second processor devices determines that respective radios are not required to send data, the determined one of the first or the second processor devices is configured to change which of the end node and the access point, the first and second radios and the first and second processor devices are configured to communicate with.

13. The apparatus of claim 12, wherein the first and second processor devices exchange communications between the processor devices using direct memory access (DMA) or other transfer methods between the processors.

14. The apparatus of claim 12, wherein the first and second processor devices each manages its own wireless communication on the side of the apparatus to which the respective processor is connected.

15. A networked detection system comprising:
   a network of sensor devices;
   a gateway to provide a network connection to connect the one or more sensor devices to the network;
   an access point in communication with the gateway; and
   a range extender for connecting the one or more sensor devices to the gateway, with the range extender comprising:
      a first radio to wirelessly communicate with the access point; a second radio to wirelessly communicate with the end node;
      a first processing device programmed to control and process messages received from the first radio, the first processing device configured to determine whether the first radio is required to send data to the access point;
      a second processing device programmed to control and process messages received from the second radio, the second processing device configured to determine whether the second radio is required to send data to the end node; and
      wherein when either one of the first and second processing devices determines that respective radios are not required to send data, the determined one of the first or the second processing devices is configured to change which of the end node and the access point, the first and second radios and the first and second processing devices are configured to communicate with.

16. The networked detection system of claim 15 wherein at least some of the sensors are constrained sensor devices and remaining ones of the sensors are a second different type of device having greater processing capabilities than the constrained sensor devices and the range extender connects the constrained sensor devices to the gateway.

17. The networked detection system of claim 15 wherein the first radio and first processing device are part of a plurality of first radios and first processing devices, which with the second radio and second processing device providing the range extender.

18. The networked detection system of claim 15 wherein the second radio and second processing device are part of a plurality of second radios and second processing devices, which with the first radio and first processing device providing the range extender.

* * * * *